United States Patent [19]
Pettiet

[11] Patent Number: 5,474,093
[45] Date of Patent: Dec. 12, 1995

[54] THUMB SUCKER TRAINING DEVICE

[76] Inventor: Monte C. Pettiet, Rte. 2, Box 494, Bridgeport, Tex. 76426-0494

[21] Appl. No.: 96,219

[22] Filed: Jul. 22, 1993

Related U.S. Application Data

[63] Continuation-in-part of Ser. No. 891,294, May 29, 1992, abandoned.

[51] Int. Cl.⁶ ..................................................... A61F 5/37
[52] U.S. Cl. .......................................... 128/880; 128/898
[58] Field of Search .................... 128/878–880, 128/898; 2/16–21, 161 R, 161 A, 167, 163, 159

[56] References Cited

U.S. PATENT DOCUMENTS

| | | | |
|---|---|---|---|
| 824,174 | 6/1906 | Clark | 128/879 |
| 1,036,017 | 8/1912 | Skaggs | 128/880 |
| 1,315,035 | 9/1919 | Post | 606/237 |
| 1,345,783 | 7/1920 | Kelly | 128/880 |
| 1,488,178 | 4/1924 | Faris | 128/881 |
| 1,794,515 | 3/1931 | Davis | 128/880 |
| 1,800,755 | 4/1931 | Roberts | 128/880 |
| 1,823,904 | 9/1931 | Kaiser | 128/880 |
| 1,929,318 | 10/1933 | Klosky | 128/880 |
| 2,072,683 | 3/1937 | Niedorff | 128/880 |
| 2,143,927 | 1/1939 | Thompson | 128/880 |
| 2,442,176 | 5/1948 | Orr | 128/880 |
| 2,498,122 | 2/1950 | Haniuk | 128/880 |
| 2,633,126 | 3/1953 | Newmark | 128/880 |
| 4,506,663 | 3/1985 | Baron | 128/880 |
| 4,653,490 | 3/1987 | Eisenberg | 128/880 |
| 4,787,376 | 11/1988 | Eisenberg | 128/880 |
| 4,873,998 | 10/1989 | Joyner | 128/880 |

FOREIGN PATENT DOCUMENTS

| 0543767 | 7/1957 | Canada | 128/880 |
|---|---|---|---|

Primary Examiner—Michael A. Brown
Attorney, Agent, or Firm—John F. Bryan, Jr.

[57] ABSTRACT

A device for retraining thumb suckers has a glove fitted to the digit with an external cover having a hard shape which impairs the normal gratification derived and an inherently unpleasant taste to displace the normally pleasant associations upon which the habit is based. Straps encircle the wrist and a lockable buckle resists all but destructive removal of the device.

1 Claim, 3 Drawing Sheets

THUMB SUCKER TRAINING DEVICE

"This is a continuation-in-part of application Ser. No. 891,294 filed on May 29, 1992, now abandoned."

FIELD OF THE INVENTION

The present invention relates to the field of thumb protectors or guards as used for the purpose of breaking children of the habit of thumb sucking and more particularly such devices incorporating positive means for preventing removal.

BACKGROUND AND SUMMARY OF THE INVENTION

The childhood habit of thumb sucking has long been recognized as a problem and many remedies have been tried over the years, with varying degrees of success. While the habit may yield to light discipline, intractable offenders who defy all reasonable measures are not uncommon. Severe orthodontic problems, which result when thumb sucking persists into later childhood, have inspired various custom devices of sometimes barbaric nature. Such "training aids" follow the teachings of Mitchell, U.S. Pat. No. 1,048,569; Rood, U.S. Pat. No. 1,633,037 and Paul, U.S. Pat. No. 2,068,109 in attempting to either physically prevent the habit or to eliminate any perceived gratification. Children, however, are capable, persistent problem solvers and learn to avoid or defeat the most elaborately expensive training aids now available. A home remedy of hot sauce or vinegar painted on the thumb, is a long standing preventive practice, and commercial solutions containing denatonium benzoate or sucrose octaacetate are also available, but sadly, in spite of all efforts, the habit may continue into puberty. The inventor has noted through extensive observation that long term control of the thumb sucking habit is seldom achieved through either the preventive measures as taught by Mitchell or the impaired gratification as taught by Rood and Paul. He has found however, that impaired gratification together with mildly unpleasant sensory stimulus provides a broadly effective retraining technique. With this technique, the prior pleasant associations are gently displaced so that the subject becomes gradually and permanently rehabituated. Another dimension of the problem lies in the fact that the subject is not disposed to cooperate with such retraining, particularly at the subconscious level, so disablement or removal the training device must be physically discouraged.

A first object of the present invention is therefore, to provide a thumb sucker retraining device which disrupts the gratification response while additionally producing mildly unpleasant sensory stimuli. A second object is to make this device resistant to efforts to either remove or disable it.

The present invention achieves these objects by providing a glove for the abused digit, usually the thumb, and covering the digit with a hard, unyielding shape having an inherent mildly unpleasant taste. The hard shape detracts from the oral aspect of gratification while the unpleasant taste introduces a negative association. Both "cures" have been employed separately in the past without systematic success but, when used together, the combination has proven consistently effective in banishing the habit. Consistent use is a primary requisite in successful retraining and, to this end, the invention may include lockable retaining means to discourage non-destructive dislocation or removal of the device.

DESCRIPTION OF THE DRAWINGS

The aforementioned and other objects and features of the invention will be apparent from the following detailed description of specific embodiments thereof, when read in conjunction with the accompanying drawings, in which.

DETAILED DESCRIPTION OF THE DRAWINGS

Figure 1:
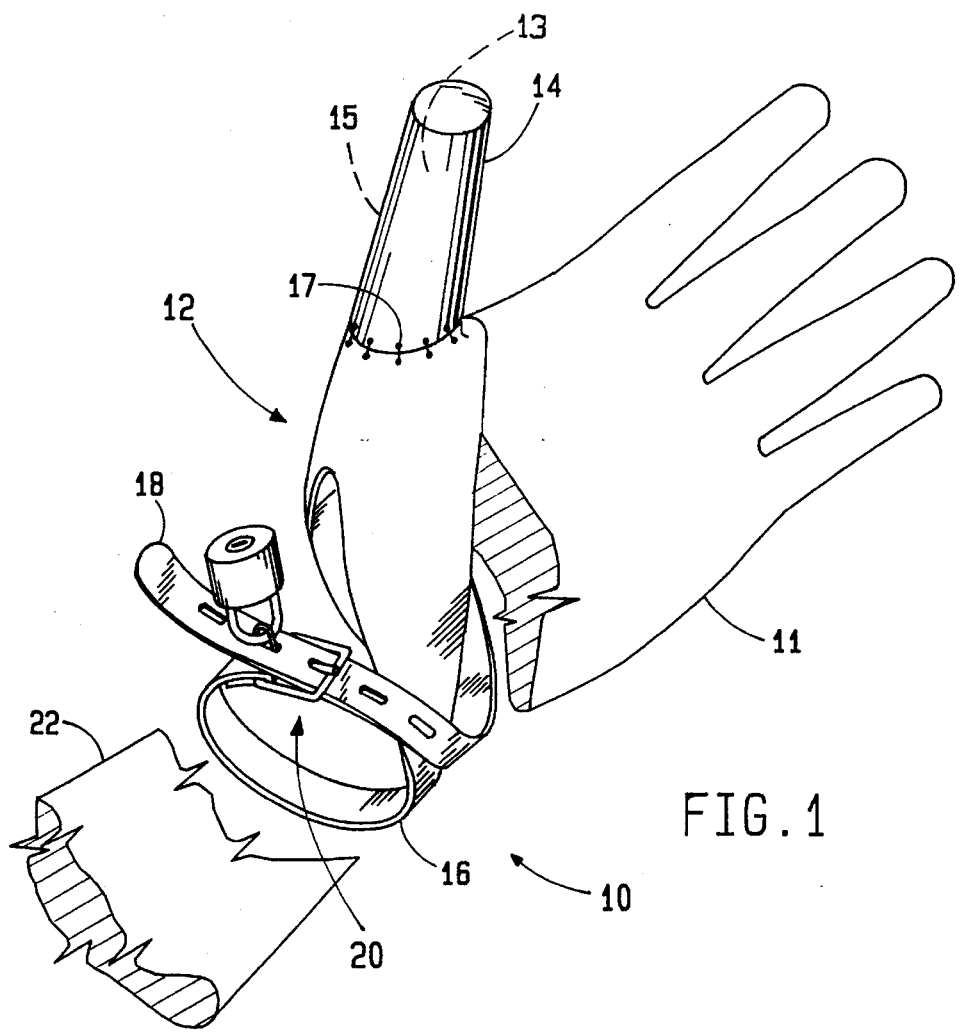
FIG. 1 is a view of a preferred embodiment of the present invention as applied to the subject.
Figure 2:
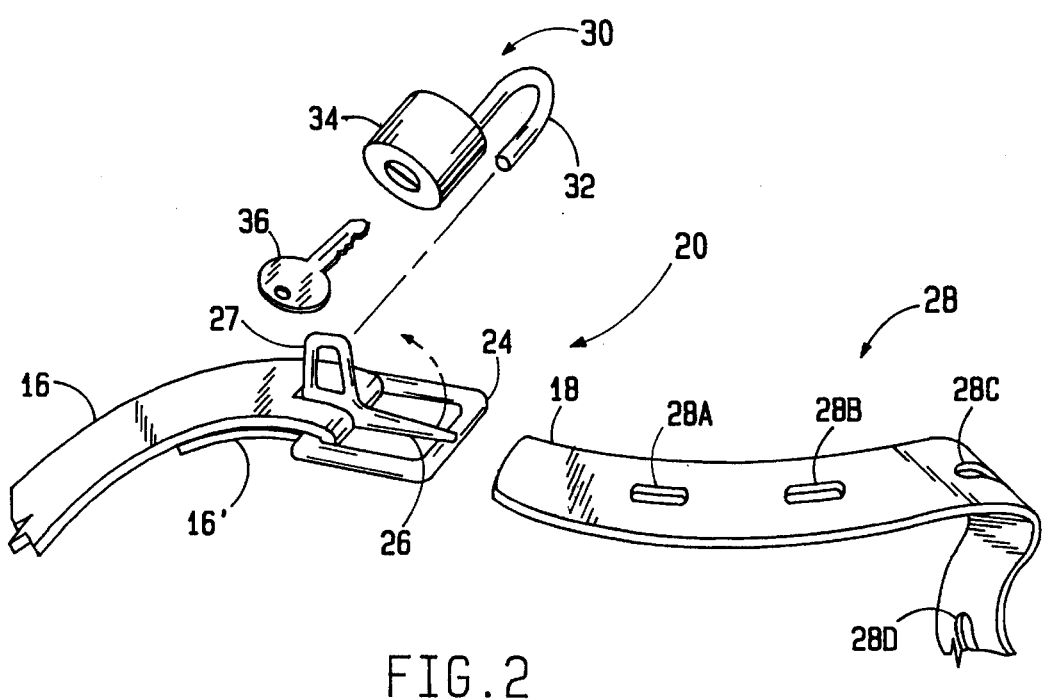
FIG. 2 is a detail view showing the buckle assembly of the embodiment of FIG. 1.

Turning now to FIG. 1, there is shown a preferred embodiment 10 of the present invention, where guard 12 fitted to the subject's hand 11 so that the thumb 13 is enclosed in the glove guard thumb 15. A hard unyielding external cover 14 is attached to guard thumb 15 by a suitable adhesive or by stitches 17. An aluminum sheath is a preferred form for cover 14 because of its hardness, corrosion resistance and inherent distasteful reaction with saliva. Other similarly reactive metals may also be used. Guard 12 includes extended straps 16 and 18 which encircle wrist 22 of the subject from opposite directions and are joined by buckle assembly 20. Thus, guard 12 is fitted in a manner which is comfortable, but not subject to accidental displacement, FIG. 2 is a view of buckle assembly 20 in greater detail and here, strap 18 is shown in position to be passed through buckle ring 24. Overlapping end 16' passes through buckle ring 24 and is sewn back to strap 16 for a permanent connection. Elongate hole 28C of a series 28 in strap 18 is engaged by hinged buckle tongue 26 when guard 12 is properly fitted. The spacing is such that the adjacent elongate hole 28B can then be fitted over eyelet 27, formed as an integral part of buckle tongue 26. Loop 32 of lock assembly 30 is passed through eyelet 27 and engaged with lock body 34, as shown in FIG. 1, thereby retaining guard 12 so that it cannot be readily removed, apart from some destructive act.

Figure 3:
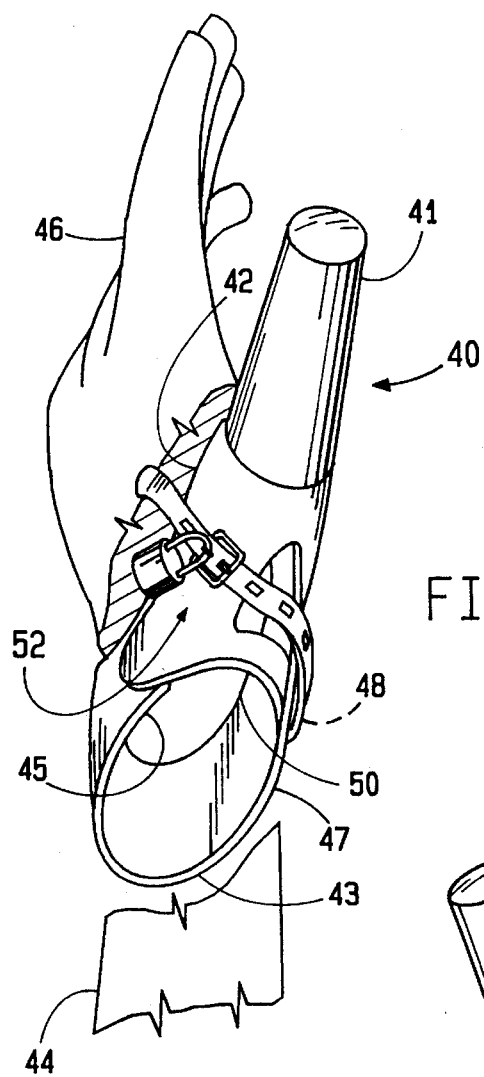
FIG. 3 is a view showing an alternate embodiment of the present invention.
Figure 4:
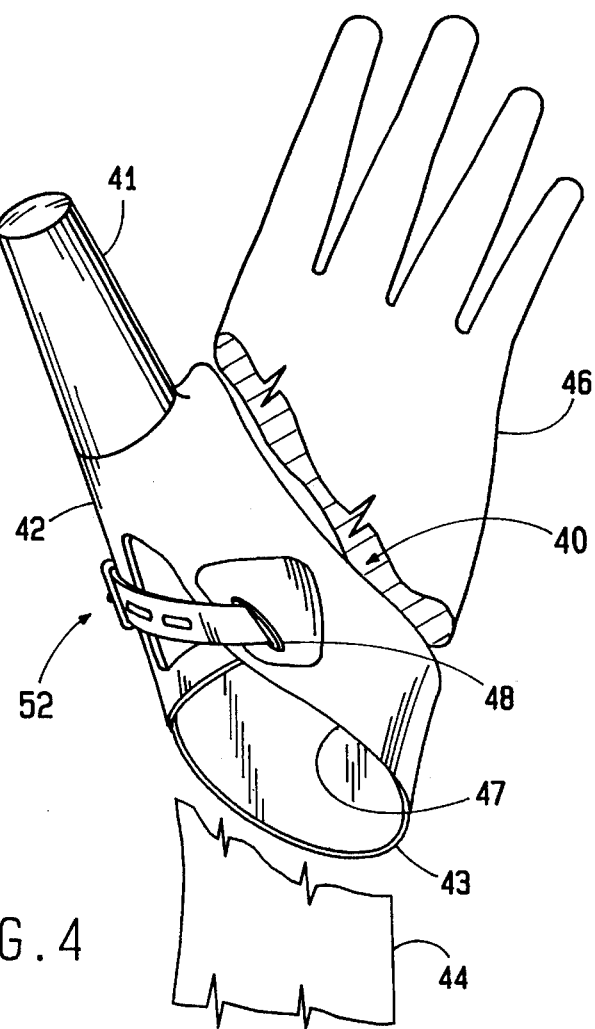
FIG. 4 is a second view of the embodiment of FIG. 3.

FIGS. 3 and 4 show an alternate embodiment 40 of the present invention as may be preferred for some custom fitted applications. Here, in the manner previously shown, guard 42 includes the unyielding shape of cover 41, but in this case is made with an integral wristlet strap 43, through which hand 46 of the subject must pass, for fitting around wrist 44. Strap 50 extends from outer portion 45 of wristlet strap 43, across the back of hand 46 and through slot 48, located on wristlet strap inner portion 47. Strap 50 is then folded back to outer portion 45, tightened and locked in place by buckle assembly 52 in the manner of FIG. 2.

Figure 5:
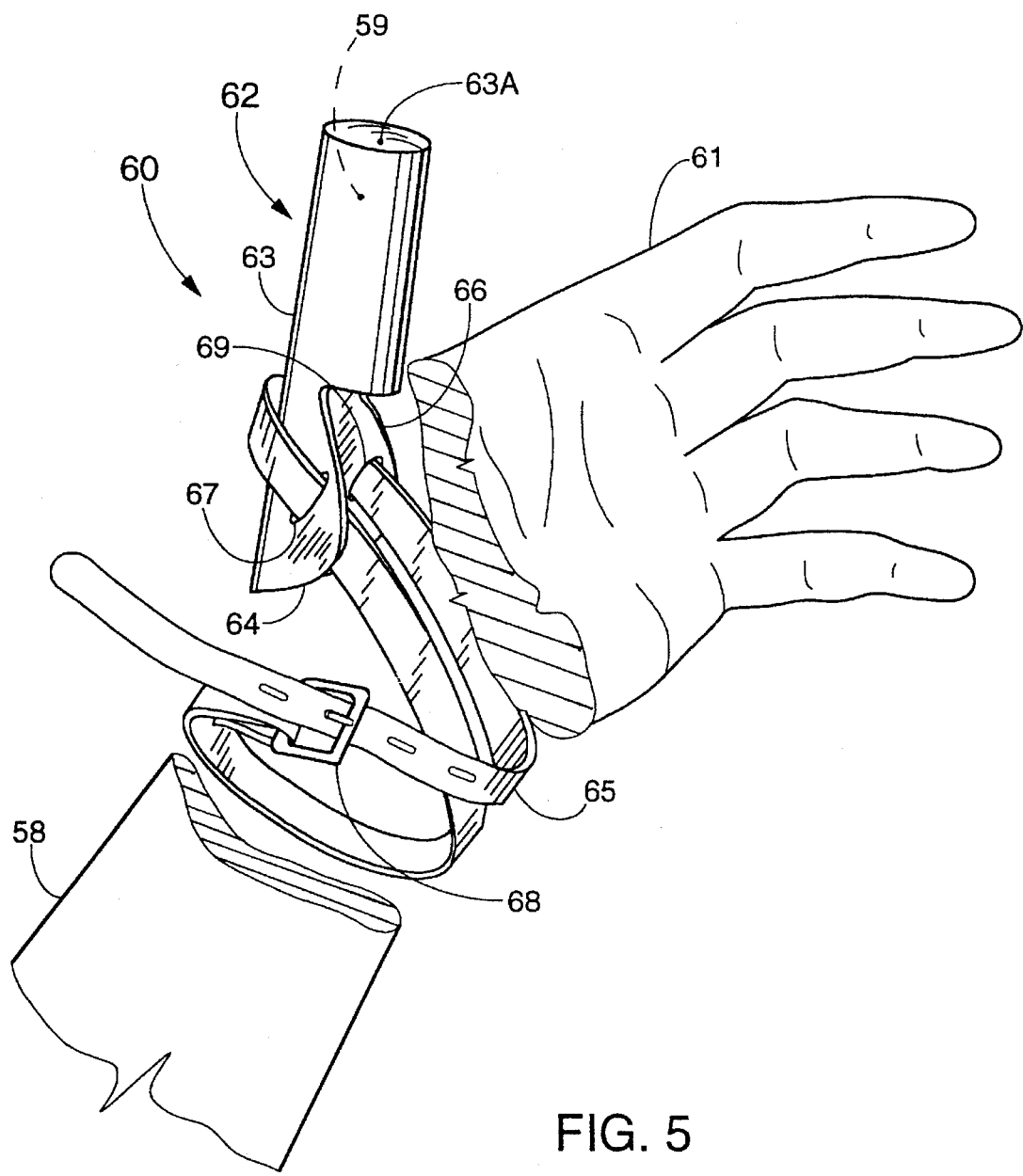
FIG. 5 is view of a second preferred embodiment of the present invention.

In FIG. 5 is shown a second preferred embodiment 60 of the present invention wherein guard 62 comprises a cylindrical aluminum sheath 63 fitted directly over thumb 59 of hand 61. The outer end 63A of aluminum sheath 63 is closed and the open inner end, through which thumb 59 extends, is formed with opposed attaching extensions 64 and 66 which include fitting slots 67 and 69 respectively. Strap assembly 65 passes through fitting slots 67 and 68 and passes around wrist 59 to be attached by buckle 68 in the manner previously disclosed. Attaching extensions 64 and 66 may be bent as required to fit the individual shape of hand 61 and may be flattened to permit fitting guard 62 to a digit other than the thumb. Thus, the unyielding shape for impairing oral gratification when inserted in the mouth and unpleasant taste reaction for building a negative association when sucked now known to be effective In retraining a habitual "thumb-sucker", are provided at the least expense.

It will be understood by those skilled in the art that changes may be made within the scope of this invention, so that it is not limited only to what is described in the drawings and specification, but is capable of rearrangement, modification and substitution of parts.

I claim:

1. A method for training a subject habituated to sucking a digit of the hand comprising the steps of:

providing a material consisting primarily of aluminum which reacts when exposed to saliva;

shaping the material in a hard shape to cover the habitually sucked digit;

covering said habitually sucked digit with said hard shape;

impairing oral gratification to the subject through contact with said hard shape when said digit is inserted in the mouth;

inducing an unpleasant taste by the reaction of saliva with aluminum when said digit is sucked; and repeating the steps of impairing and inducing whenever the subject is moved to so insert and suck said digit.

* * * * *